United States Patent [19]

Wei et al.

[11] Patent Number: 4,997,962

[45] Date of Patent: Mar. 5, 1991

[54] SYNTHESIS OF TETRATHIOPERRHENATE SALTS

[75] Inventors: Liwen Wei, Somerville; Thomas R. Halbert, Annandale; Edward I. Stiefel, Bridgewater, all of N.J.

[73] Assignee: Exxon Research and Engineering Company, Florham Park, N.J.

[21] Appl. No.: 202,342

[22] Filed: Jun. 6, 1988

[51] Int. Cl.$^5$ ............................................ C07F 13/00
[52] U.S. Cl. ...................................................... 556/45
[58] Field of Search ........................................ 556/45

[56] References Cited

U.S. PATENT DOCUMENTS 2,634,280  4/1953  Tribalat et al. ...................... 556/45

OTHER PUBLICATIONS

Müller, A. et al., Z. Anorg. Allg. Chem., vol. 554, 1987, pp. 61–78 (English translation of p. 62 provided).
Roberts & Caserio, *Basic Principles of Organic Chemistry*, 2nd. edition, 1977, p. 239.

Primary Examiner—Gary P. Straub
Assistant Examiner—Stuart L. Hendrikson
Attorney, Agent, or Firm—Joseph J. Dvorak

[57] ABSTRACT

According to the present invention, an improved method for preparing tetrathioperrhenate salts is provided. Basically, a water soluble, oxygen-containing rhenium compound such as rhenium oxide or a salt containing an oxyanion of rhenium, such as $ReO_4^-$, is contacted with an aqueous ammonium sulfide or polysulfide solution in the presence of a cation which is capable of forming an aqueous insoluble salt with tetrathioperrhenate.

10 Claims, No Drawings

SYNTHESIS OF TETRATHIOPERRHENATE SALTS

FIELD OF THE INVENTION

This invention relates to an improved method for preparing salts containing a tetrathioperrhenate anion.

BACKGROUND OF THE INVENTION

The preparation of salts containing the tetrathioperrhenate anion was first reported in 1931. See, Feit, W., *Angew. Chem.* 1931, 44, p. 65). Other preparative techniques have subsequently been reported. See, for example, Müller, et al., *Chem. Ber.* 1970, 103, p. 2961, which calls for bubbling hydrogen sulfide through a dilute solution of $ReO_4^-$ in aqueous ammonium hydroxide, and Müller, et al., *Chimia* 1986, 40, p. 50, which calls for adding $Re_2O_7$ to a methanol polysulfide solution which is heated and allowed to stand for one to two days. None of these reported procedures are especially suitable for the preparation of significant quantities of tetrathioperrhenate salts, however, because of the poor yields obtained, the length of time that is required in carrying the reaction, or indeed the complexity of preparation of the reagents employed in the synthetic procedure.

SUMMARY OF THE INVENTION

According to the present invention, an improved method for preparing tetrathioperrhenate salts is provided. Basically, a water soluble, oxygen-containing rhenium compound such as rhenium oxide or a salt containing an oxyanion of rhenium, such as $ReO_4^-$, is contacted with an aqueous ammonium sulfide or polysulfide solution in the presence of a cation which is capable of forming an aqueous insoluble salt with tetrathioperrhenate.

In a particularly preferred embodiment of the present invention, a perrhenate salt, such as ammonium perrhenate, is added to an aqueous ammonium polysulfide solution (composed of sulfur added to aqueous ammonium hydrogen sulfide) in the presence of a cation which is capable of forming a salt of tetrathioperrhenate that is insoluble in the aqueous phase. Examples of such cations capable of forming aqueous insoluble salts with tetrathioperrhenate include tetraethyl ammonium cation, tetraphenyl phosphonium and tetraphenyl arsonium cations. These cations can be added to the aqueous solution in the form of the corresponding halides.

These and other features of the present invention will be better understood upon the reading of the "Detailed Description" which follows.

DESCRIPTION OF THE PREFERRED EMBODIMENTS

The invention encompasses an improved method of preparing tetrathioperrhenate salts by adding a rhenium oxide or a salt containing an oxyanion of rhenium to an aqueous ammonium sulfide or polysulfide solution in the presence of a cation which is capable of forming an aqueous insoluble tetrathioperrhenate.

Compounds containing rhenium that are particularly suitable as starting materials in the practice of the present invention include ammonium perrhenate, potassium perrhenate and dirhenium heptaoxide. Especially preferred is ammonium perrhenate.

As indicated, the rhenium-containing starting material is added to an aqueous ammonium sulfide or polysulfide solution. An especially preferred solution contains an additional amount of sulfur at least equal to the stoichiometric amount of sulfur required to convert the perrhenate to the tetrathioperrhenate material, and preferably an excess amount of sulfur. In general, the aqueous solution will have a pH of between about 8 and 11, with a pH in the range of about 9 to 10 being preferred.

As stated previously, in the practice of the present invention the rhenium-containing starting material is added to the aqueous ammonium sulfide or polysulfide solution in the presence of a cation which is capable of forming an aqueous insoluble salt with tetrathioperrhenate anion. In general, such cations include tetra-alkyl, tetra-aryl, and tetra-aralkyl ammonium ions, tetra-aryl phosphonium and arsonium ions. Cations that are particularly preferred in the present invention include tetraethyl ammonium, benzyl triethyl ammonium, tetraphenyl phosphonium and tetraphenyl arsonium cations. These materials are added to the aqueous solution in the form of their halides, especially bromides, although other salts containing these cations may be employed.

The addition of the rhenium-containing starting material to the aqueous ammonium sulfide or polysulfide solution may be conducted over a wide temperature range. In general, however, ambient temperature is quite satisfactory.

After addition of the rhenium-containing starting material to the ammonium sulfide or polysulfide solution, the reaction mixture is mixed for a time sufficient to complete the formation of the tetrathioperrhenate salt. This reaction time will vary according to pH, sulfide/polysulfide concentration and Re concentration. Since the tetrathioperrhenate salt is insoluble in the aqueous phase, visual observation of the amount of precipitate formed gives a qualitative indication of the extent of reaction.

While not wishing to be bound by any theory, it is believed that aqueous solutions of tetrathioperrhenate anion tend to undergo oligomerization and polymerization to $Re_2S_7$ and related compounds, accounting for the poor yields and difficulty of preparation of tetrathioperrhenate reported by previous workers. In the practice of the present invention, since the reaction is conducted in the presence of a cation that forms an insoluble tetrathioperrhenate salt, the tetrathioperrhenate anion apparently precipitates from the solution upon formation, thereby avoiding or suppressing the oligomerization or polymerization of tetrathioperrhenate, thereby enhancing the yields that can be obtained according to the process of the present invention. Also, the preparative procedure disclosed herein is simple, direct and not based on difficult-to-prepare starting materials.

The tetrathioperrhenate salts obtained in the practice of the present invention, of course, are useful as precursors for rhenium sulfide heterogeneous catalysts such as rhenium sulfide catalysts used in the catalytic dehydropolymerization of tetrahydroquinoline.

The following examples illustrate the invention, but are not intended to limit it in any way.

EXAMPLES

Example 1

This example illustrates the synthesis of tetraethyl ammonium tetrathioperrhenate. To an aqueous ammonium sulfide solution (400 ml containing 9 to 10 weight percent sulfur) was added 20 g of tetraethyl ammonium bromide and 10 g of additional sulfur. Then 20 g of ammonium perrhenate was added to solution at room temperature. The resulting mixture was stirred for eight hours and filtered. The precipitate was thoroughly washed with water, methanol and ether, and air dried to yield 29.5 g of tetraethyl ammonium tetrathioperrhenate (89 percent yield). The identity of the material was established by IR, UV-Vis, X-ray powder pattern and elemental analysis.

Example 2 and 3

In these examples the procedure of Example 1 was followed except that in one instance benzyl triethyl ammonium bromide was used in lieu of the tetraethyl ammonium bromide and in the other instance tetraphenyl arsonium chloride was used. The identity of the precipitated tetrathioperrhenate salt, in each instance, was established by IR and UV-Vis analysis.

It should be understood that the foregoing disclosure, description and examples are illustrative of the invention. Various changes in the details of the invention will be apparent to those with skill in the art, and may be made within the scope of the appended claims without departing from the spirit of the present invention.

What is claimed is:

1. A method of preparing a salt containing the tetrathioperrhenate anion comprising: contacting a rhenium compound selected from rhenium oxide and water soluble salts containing an oxy-anion of rhenium with a sulfur containing solution selected from aqueous ammonium sulfide and aqueous ammonium polysulfide solutions, the contacting being in the presence of a cation capable of forming a water insoluble salt with tetrathioperrhenate, and said contacting being for a time sufficient to form said water insoluble salt containing the tetrathioperrhenate anion.

2. The method of claim 1 wherein said rhenium compound is selected from rhenium oxide and perrhenate salts.

3. The method of claim 2 wherein said rhenium compound is a perrhenate salt.

4. The method of claim 2 wherein the solution is an aqueous ammonium sulfide solution.

5. The method of claim 4 wherein the solution has a pH in the range of about 8 to about 11.

6. The method of claim 5 wherein the solution has a pH in the range of about 9 to about 10.

7. The method of claim 5 wherein the cation is selected from tetra-alkyl, tetra-aryl and tetra-aralkyl ammonium, tetra-aryl phosphonium and arsonium cations.

8. The method of claim 5 wherein the cation is selected from tetraethyl ammonium, benzyl triethyl ammonium, tetraphenyl phosphonium and tetraphenyl arsonium.

9. A method of preparing a salt containing the tetrathioperrhenate anion comprising: adding a rhenium compound selected from rhenium oxide and water soluble salts containing an oxy-anion of rhenium to an aqueous solution selected from ammonium sulfide and ammonium polysulfide, said solution having a pH in the range of about 8 to about 11, said solution containing a salt containing a cation capable of forming an aqueous insoluble salt with tetrathioperrhenate anion and mixing said added rhenium compound and aqueous solution for a time sufficient to form said insoluble slat containing said tetrathioperrhenate anion, whereby said salt precipitates from solution.

10. The method of claim 9 wherein said salt containing a cation capable of forming an insoluble salt with tetrathioperrhenate anion is a cation selected from the group consisting of tetraethyl ammonium, benzyl triethyl ammonium, tetraphenyl phosphonium and tetraphenyl arsonium cations.

* * * * *